United States Patent [19]

Ho et al.

[11] 3,968,247

[45] July 6, 1976

[54] SUBSTITUTED OR UNSUBSTITUTED P-ALKANOYL TOLUENES AS ANTI-DIABETIC AGENTS

[75] Inventors: Robert S. Ho, Denville; William J. Houlihan, Mountain Lakes; Jeffrey Nadelson, Lake Parsippany, all of N.J.

[73] Assignee: Sandoz, Inc., E. Hanover, N.J.

[22] Filed: Aug. 20, 1975

[21] Appl. No.: 605,973

Related U.S. Application Data

[60] Division of Ser. No. 546,756, Feb. 3, 1975, Pat. No. 3,924,003, which is a continuation-in-part of Ser. No. 445,265, Feb. 25, 1974, abandoned.

[52] U.S. Cl. ............................................. 424/331
[51] Int. Cl.$^2$ ...................................... A61K 31/12
[58] Field of Search .................................. 424/331

[56] References Cited

OTHER PUBLICATIONS

Tsatas, Chemical Abstracts 74:42099x (1971).
Ropp et al., Chemical Abstracts 53;6174c (1959).
Pearson et al., Chemical Abstracts 50:4070b (1956).
Landrum et al., Chemical Abstracts 49:15791g (1955).
Landrum et al., Chemical Abstracts 48:13655c (1954).

*Primary Examiner*—Norman A. Drezin
*Attorney, Agent, or Firm*—Gerald D. Sharkin; Robert S. Honor

[57] ABSTRACT

Certain substituted or unsubstituted p-alkanoyl toluenes, e.g., p-alkanoyl toluene, are useful as anti-obesity and anti-diabetic agents.

5 Claims, No Drawings

SUBSTITUTED OR UNSUBSTITUTED P-ALKANOYL TOLUENES AS ANTI-DIABETIC AGENTS

This is a division of application Ser. No. 546,756 filed Feb. 3, 1975 now U.S. Pat. No. 3,924,003, which, in turn, is a continuation-in-part of Ser. No. 445,265, filed Feb. 25, 1974, now abandoned.

This invention relates to the pharmaceutical activity of p-alkanoyl toluenes. More particularly, this invention concerns the use of substituted or unsubstituted p-alkanoyl toluenes in the treatment of obesity and diabetes. The invention also relates to pharmaceutical compositions containing these compounds as an active ingredient thereof.

The active agents with which this invention is concerned may be represented by the following structural formula:

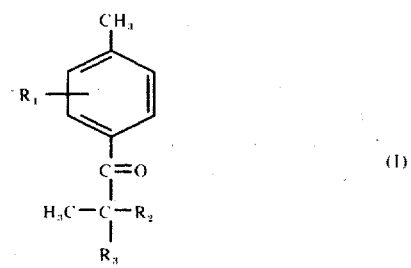

where
$R_1$ represents hydrogen, halo having an atomic weight of about 19 to 36, and straight chain lower alkoxy, i.e., straight chain alkoxy having 1 to 4 carbon atoms, e.g., methoxy, ethoxy, isopropoxy or the like, and $R_2$ and $R_3$ each independently represent alkyl having 1 or 2 carbon atoms, i.e., methyl or ethyl.

The compounds of formula (I) above are known and may be prepared according to methods disclosed in the literature from known materials. The present invention contemplates only the novel use of such compounds as anti-obesity and anti-diabetic agents.

The compounds of formula (I) are useful because they possess pharmacological activity in animals. In particular, the compounds of formula (I) are useful as anti-obesity agents in the treatment of obesity as indicated by (1) preventing an increase in the blood sugar level in male Wistar rats in groups of 4 which have fasted for 16 hours and then are given an initial dose of 200 milligrams per kilogram of animal body weight of the test compound orally. One hour later, the rats are given 2 grams per kilogram of animal body weight of maltose load. Fifteen minutes after administration of the maltose, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently, and by (2) preventing an increase in the blood sugar level in male Wistar rats in groups of four which are fasted for 16 hours and then are given an initial dose of 200 milligrams per kilogram of animal body weight of the test compound orally. One hour later, the rats are given 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently. The blood sugar levels are calculated and compared to the control.

The compounds of formula (I) are also useful as juvenile anti-diabetic agents in the treatment of diabetes in adults as indicated by the lowering of blood glucose in 6 to 8-week old male Royal Hart mice weighing 30 to 35 grams which are fasted in groups of 5 for 16 hours and then are given an initial dose of 200 milligrams per kilogram of animal body weight of the compound orally. One and one-half hours later, the mice are given orally 2 grams per kilogram of animal body weight of a glucose challenge. Twenty-five minutes later, the mice are anesthetized with 85 milligrams per kilogram of animal body weight of sodium hexobarbital and 5 minutes later blood is collected via cardiac puncture. The blood samples are placed in an autoanalyzer cup containing 0.025 milliliters of heparin (1,000 units per milliliter); and the samples are capped, shaken, and stored in ice. The glucose content is determined by the autoanalyzer potassium ferric-cyanide N-2b method and are compared with a control group, which receives orally 0.5% carboxmethyl cellulose vehicle and are run concurrently.

For such uses, the compounds of formula (I) may be administered orally or parenterally as such or admixed with conventional pharmaceutical carriers. They may be administered orally in such forms as tablets, dispersible powders, capsules, soft gelatin capsules, preferably soft gelatin capsules, and emulsions, and parenterally as emulsions, e.g., a sterile injectable emulsion. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, lubricating agents, e.g., magnesium stearate, stearic acid and talc, and absorbing agents such as colloidal silicone dioxide. The tablets may be uncoated or coated by known techniques to delay disintegration and absorption in the gastro-intestinal tract and thereby provide a sustained action over a longer period. Similarly, suspensions, and emulsions may contain the active ingredient in admixture with any of the conventional excipients utilized by the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient admixed with an inert solid diluent, e.g., calcium carbonate, calcium phosphate and kaolin. Soft gelatin capsules may contain the active ingredient in admixture with conventional pharmaceutical excipients, e.g., inert carriers such as vegetable oils (soybean oil, corn oil and the like) polyethyleneglycol derivatives or mineral oils. The injectable compositions are formulated as known in the art. These pharmaceutical preparations may contain up to about 90% of the active ingredient in combination with the carrier or adjuvant.

The anti-obesity effective dosage of active ingredient employed for the treatment of obesity and the anti-diabetic effective amount of active ingredient employed in the treatment of diabetes may vary depending on the particular compound employed, the mode of administration and the severity of the condition being treated. However, in general, satisfactory results are obtained for both the hypolipodemia effect and the anti-diabetic effect when the compounds of formula (I) are administered at a daily dosage of from about 1 milligram to about 200 milligrams per kilogram of animal body weight, p.o., preferably given in divided doses two to four times a day, or in sustained release form. For most large mammals, the total daily dosage for both indications is from about 75 to about 1500 milligrams. Dosage forms suitable for internal use comprise from about 20 to about 750 milligrams of the active compound in intimate admixture with a solid or liquid pharmaceutically acceptable carrier or diluent.

Compounds of formula (I) which can be used as the active ingredient include the following:
a. 2-chloro-4-pivaloyl toluene
b. 2-methoxy-4-pivaloyl toluene, or
c. p-pivaloyl toluene, the latter being especially preferred.

A representative formulation suitable for oral administration is a tablet, capsule or soft gelatin capsule prepared by standard tabletting or encapsulating techniques which contains the following and may be administered 2 to 4 times a day in the treatment of obesity or diabetes.

EXAMPLE 1

| Ingredient | Weight (mg.) Capsule |
|---|---|
| p-pivaloyl toluene | 100 |
| tragacanth | — |
| lactose | 300 |

| Ingredient | Weight (mg.) Capsule |
|---|---|
| corn starch | — |
| talcum | — |
| magnesium stearate | — |
|  | 400 mg. |

EXAMPLE 2

| Ingredient | Weight (mg.) tablet | capsule | soft gelatin capsule |
|---|---|---|---|
| p-pivaloyl toluene | 100 | 100 | 100 |
| polyvinylpyrrolidone | 15 | — | — |
| lactose | 282.5 | 346 | — |
| corn starch | 25 | — | — |
| talcum | 15 | — | — |
| colloidal silicon dioxide | 50 | 50 | — |
| magnesium stearate | 2.5 | — | — |
| stearic acid | — | 4 | — |
| soybean oil | — | — | 300 |
|  | 500 mg. | 500 mg. | 400 mg. |

The following pharmaceutical compositions are formulated with the indicated amount of active agent using conventional techniques. The injectable emulsion, the oral liquid suspension, and the oral liquid emulsion represent formulations useful as unit doses and may be administered in the treatment of obesity or diabetes. The injectable emulsion is suitable for administration once or twice a day whereas the oral liquid suspension and the oral liquid emulsion is suitably administered 2 to 4 times per day for this purpose.

EXAMPLE 3

| Ingredient | Weight (mg.) Oral liquid suspension |
|---|---|
| p-pivaloyl toluene | 100 |
| magnesium aluminum silicate | 47.5 |
| flavor | q.s. |
| color | q.s. |
| methyl paraben, U.S.P. | 4.5 |
| propyl paraben, U.S.P. | 1.0 |
| polysorbate 80 (e.g., Tween 80), U.S.P. | 5 |
| sorbitol solution, 70%, U.S.P. | 2,500 |
| buffer agent to adjust pH for desired stability | q.s. |
| water | q.s. to 5 ml. |

EXAMPLE 4

| Ingredient | Weight (mg.) Sterile injectable emulsion | Oral liquid emulsion |
|---|---|---|
| p-pivaloyl toluene | 200 | 100 |
| sodium, carboxy methylcellulose, U.S.P. | — | 12.5 |
| polyvinylpyrrolidone | 5 | — |
| benzoyl alcohol | 0.01 | — |
| sodium chloride | to be adjusted to an isotonic concentration | — |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | 1 | 5 |
| sorbitol solution, 70% U.S.P. | — | 2,500 |
| buffer agent to adjust pH for desired stability | q.s. | q.s. |
| water | for injection q.s. to 1 ml. | q.s. to 5 ml. |

The preferred pharmaceutical compositions from the standpoint of preparation and ease of administration are soft gelatin capsules containing from about 100 to 200 milligrams of the active ingredient.

What is claimed is:

1. A method for treating diabetes which comprises administering to a mammal in need of said treatment an anti-diabetic effective amount of a compound of the formula

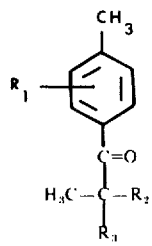

where
R₁ represents hydrogen, halo having an atomic weight of about 19 to 36, or straight chain lower alkoxy, and
R₂ and R₃ each independently represent alkyl having 1 to 2 carbon atoms.

2. The method of claim 1 in which the compound is:

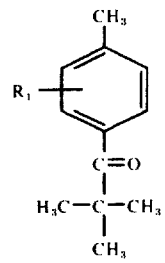

3. The method of claim 1 in which the compound is p-pivaloyl toluene.

4. The method of claim 1 wherein the compound is administered orally at a daily dosage of from about 75 milligrams to about 1500 milligrams.

5. The method of claim 1 wherein the compound is orally administered in a unit dosage form comprising from about 20 milligrams to about 750 milligrams per unit dosage.

* * * * *